US012765949B2

(12) United States Patent
Qian et al.

(10) Patent No.: US 12,765,949 B2
(45) Date of Patent: Oct. 20, 2026

(54) BUFFER ZONE FOR ALIGNMENT

(71) Applicant: Medivis, Inc., New York, NY (US)

(72) Inventors: Long Qian, Brooklyn, NY (US); Osamah Choudhry, New York, NY (US); Christopher Morley, New York, NY (US)

(73) Assignee: Medivis, Inc., New York, NY (US)

( * ) Notice: Subject to any disclaimer, the term of this patent is extended or adjusted under 35 U.S.C. 154(b) by 98 days.

(21) Appl. No.: 18/765,599

(22) Filed: Jul. 8, 2024

(65) Prior Publication Data

US 2024/0407856 A1 Dec. 12, 2024

Related U.S. Application Data

(63) Continuation-in-part of application No. 18/208,136, filed on Jun. 9, 2023, now Pat. No. 12,551,283.

(51) Int. Cl.

| | |
|---|---|
| ***G06T 19/00*** | (2011.01) |
| ***A61B 34/20*** | (2016.01) |
| ***A61B 90/00*** | (2016.01) |
| ***G06T 7/20*** | (2017.01) |
| ***G06T 7/70*** | (2017.01) |
| *A61B 34/10* | (2016.01) |

(52) U.S. Cl.

CPC .............. *A61B 34/20* (2016.02); *A61B 90/37* (2016.02); *G06T 7/20* (2013.01); *G06T 7/70* (2017.01); *G06T 19/006* (2013.01); *A61B 2034/107* (2016.02); *A61B 2090/365* (2016.02); *G06T 2207/30004* (2013.01); *G06T 2207/30241* (2013.01)

(58) Field of Classification Search

None

See application file for complete search history.

(56) References Cited

U.S. PATENT DOCUMENTS

2017/0312031 A1* 11/2017 Amanatullah ......... A61B 34/10
2018/0256256 A1* 9/2018 May ....................... A61B 34/10

* cited by examiner

*Primary Examiner* — Nicholas R Wilson

(74) *Attorney, Agent, or Firm* — Cognition IP, P.C.; Edward Steakley; Saleh Kaihani

(57) ABSTRACT

Various embodiments of an apparatus, methods, systems and computer program products described herein are directed to a Buffer Zone Engine renders a dynamic navigation guide virtual object ("dynamic navigation guide"). The Buffer Zone Engine detects changes in at least one of an instrument angular distance and an instrument position of a physical instrument in a unified three-dimensional (3D) coordinate space. The Buffer Zone Engine determines the detected change(s) corresponds to a threshold amount of difference away from the proper alignment of the physical instrument, the proper alignment representing alignment of the physical instrument with a virtual trajectory towards a target point. The Buffer Zone Engine triggers display of a first visual characteristic of the dynamic navigation guide in response to determining the detected change(s) corresponds to the threshold amount of difference away from the proper alignment.

20 Claims, 8 Drawing Sheets

600

400

BUFFER ZONE FOR ALIGNMENT

CROSS REFERENCE TO RELATED APPLICATIONS

This application is a continuation-in-part of U.S. patent application Ser. No. 18,208,136, filed on Jun. 9, 2023, and titled "Surgical Navigation Trajectory in Augmented Reality Display," which is herein incorporated by reference in its entirety.

BACKGROUND

Current conventional systems have limitations with regard to two-dimensional (2D) and three-dimensional (3D) images in surgical settings. Surgical planning and surgical navigation are necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Various embodiments of an apparatus, methods, systems and computer program products described herein are directed to a Buffer Zone Engine. The Buffer Zone Engine provides significant improvements over the limitations of conventional systems. The Buffer Zone Engine a dynamic navigation guide virtual object ("dynamic navigation guide"). The Buffer Zone Engine detects changes in at least one of an instrument angular distance and an instrument position of a physical instrument in a unified three-dimensional (3D) coordinate space. The Buffer Zone Engine determines the detected change(s) corresponds to a threshold amount of difference away from a proper alignment of the physical instrument, the proper alignment representing alignment of the physical instrument with a virtual trajectory towards a target point. The Buffer Zone Engine triggers display of a first visual characteristic of the dynamic navigation guide in response to determining the detected change (s) corresponds to the threshold amount of difference away from the proper alignment.

It is understood that, for purposes of determining whether a physical instrument is aligned with a virtual trajectory for purposes of triggering a visual characteristic, the Buffer Zone Engine analyzes an instrument's current angular distance in comparison to an angular distance required to be in alignment with the virtual trajectory. An angular distance may be based on a projected distance from a current placement of a physical instrument to the virtual trajectory. In various embodiments, an angular distance, for the purpose of determining alignment with the virtual trajectory, is based on an angular difference between at least one axis of the instrument at its current placement (or orientation) and a corresponding axis of the virtual trajectory. The Buffer Zone Engine further analyzes an instrument's position as being a distance between the instrument's tip to the virtual trajectory's line (or path). That is, the Buffer Zone detects alignment between the physical instrument and the virtual trajectory's line (or path) when the Buffer Zone Engine detects that there is no distance between a current position of the physical instrument's tip and the virtual trajectory's line (or path).

According to various embodiments, the threshold amount of difference away from proper alignment with the virtual trajectory is defined according to a buffer zone that is further defined as being part of (or within) an alignment zone.

Display of the first visual characteristic of the dynamic navigation guide thereby acts as a visual prompt in the AR display indicating physical instrument is still in the alignment zone but the Buffer Zone Engine detects that physical instrument is in the buffer zone due to the instrument's current angular distance and/or position. Since the physical instrument is in the buffer zone portion of the alignment zone, the physical instrument is not yet misaligned with the virtual trajectory.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1A:
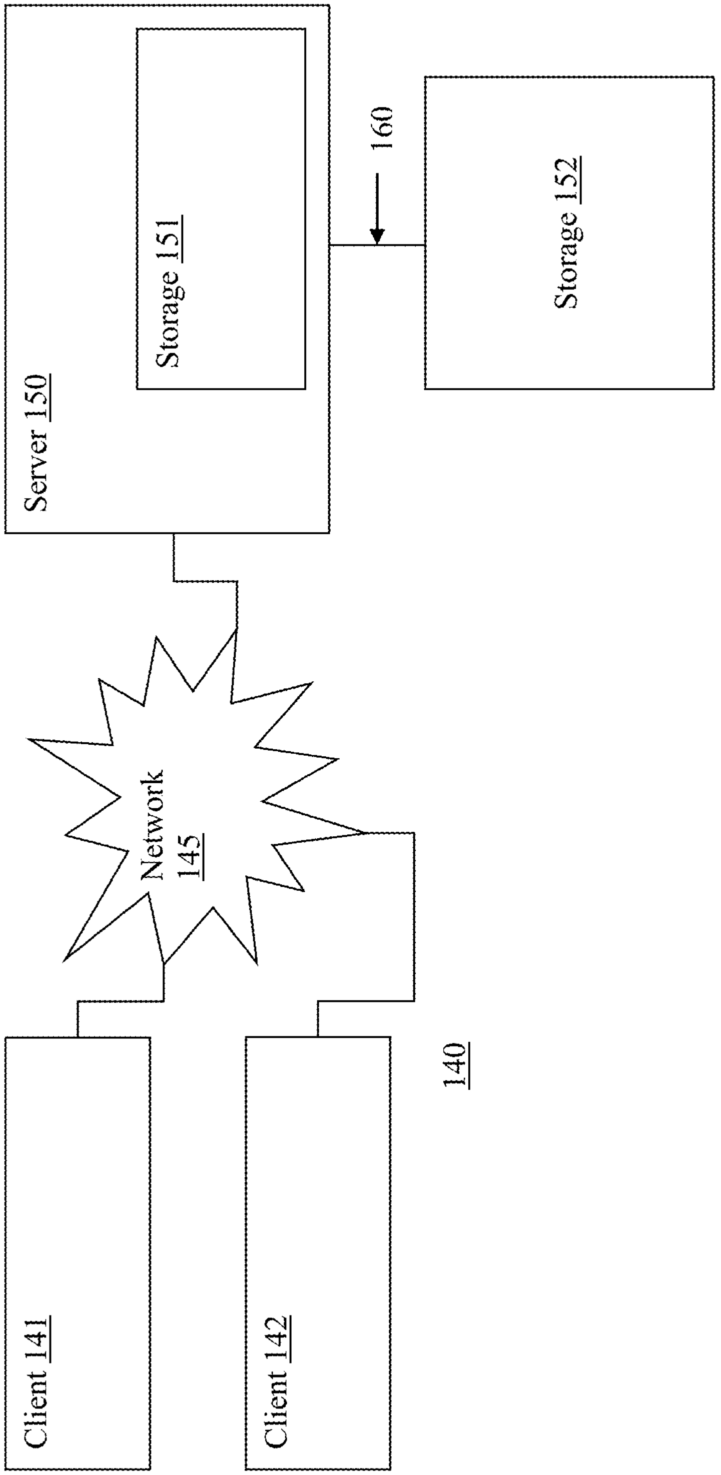
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
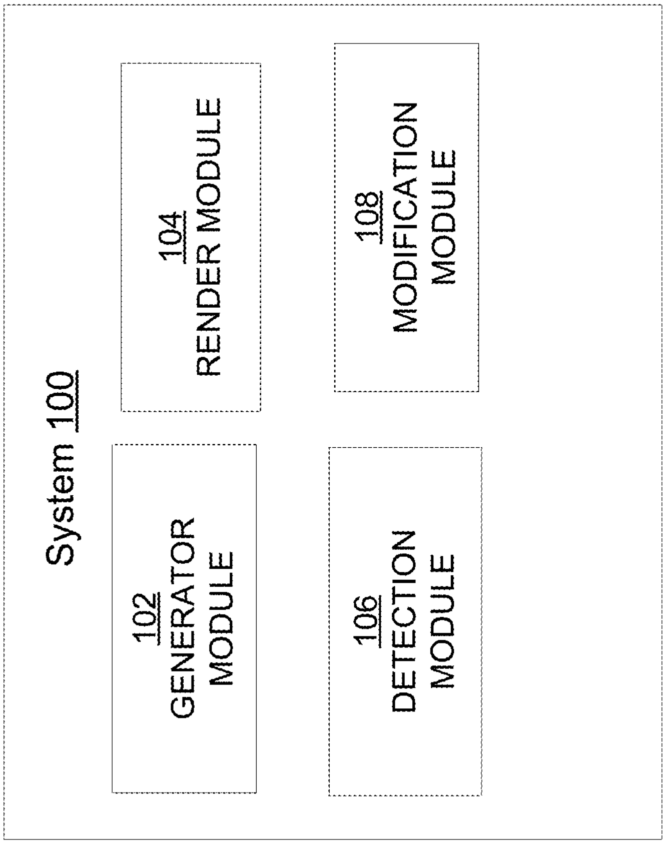
FIG. 1B is a diagram illustrating an exemplary environment in which some embodiments may operate.
Figure 2:
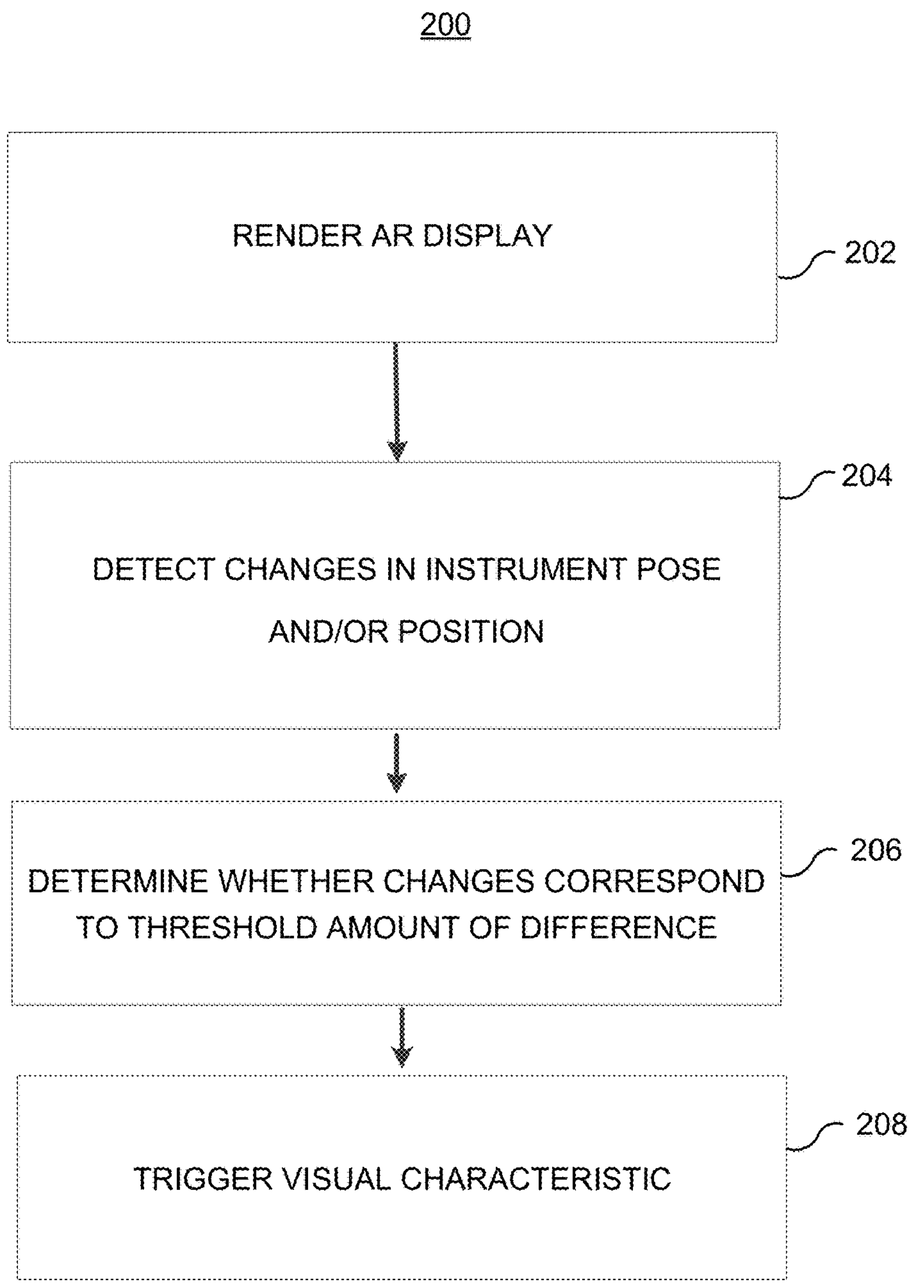
FIG. 2 is a diagram illustrating an exemplary method that may be performed in some embodiments.

FIG. 1B illustrates a block diagram of an example system 100 for a Buffer Zone Engine that includes one or more modules. The system 100 may communicate with a user device 140 to display output, via a user interface 144 generated by an application engine. In various embodiments, the user device 140 may be an AR display headset device that further includes one or more of the respective modules 102, 104, 106, 108.

A generator module 102 of the system 100 may perform functionality, steps, operations, commands and/or instructions as illustrated in one or more of FIGS. 2, 3, 4, 5 and 6 ("2-6"). The generator module 102 may generating within a unified three-dimensional (3D) coordinate space: a 3D virtual medical model positioned according to a model pose, a virtual trajectory extending from a target point associated with a selected portion of the 3D virtual medical model and a dynamic navigation guide virtual object ("dynamic navigation guide").

The render module 104 of the system 100 may perform functionality, steps, operations, commands and/or instructions as illustrated in one or more of FIGS. 2-6. The render module 104 may render an Augmented Reality (AR) display that includes concurrent display at least of the 3D virtual medical model, the target point, the virtual trajectory and the dynamic navigation guide;

The detection module 106 of the system 100 may perform functionality, steps, operations, commands and/or instructions as illustrated in one or more of FIGS. 2-6. The detection module 106 may detect one or more changes in an instrument pose and an instrument position of a physical instrument in the 3D coordinate space The modification module 108 of the system 100 may perform functionality, steps, operations, commands and/or instructions as illustrated in one or more of FIGS. 2-6. The modification module 108 may modify the display of the dynamic navigation guide in the AR display at least in part on one or more of: the instrument pose changes and the instrument position changes.

A database associated with the system 100 maintains information, such as 3D medical model data, in a manner the promotes retrieval and storage efficiency and/or data security. In addition, the model data may include rendering parameters, such as data based on selections and modifications to a 3D virtual representation of a medical model rendered for a previous Augmented Reality display. In various embodiments, one or more rendering parameters may be preloaded as a default value for a rendering parameter in a newly initiated session of the Buffer Zone Engine.

In various embodiments, the Buffer Zone Engine accesses one or more storage locations that contain respective portions of medical model data. The medical model data may be represented according to two-dimensional (2D) and three-dimensional (3D) medical model data. The 2D and/or 3D ("2D/3D") medical model data 124 may include a plurality of slice layers of medical data associated with external and internal anatomies. For example, the 2D/3D medical model data 124 may include a plurality of slice layers of medical data for generating renderings of external and internal anatomical regions of a user's head, brain and skull. It is understood that various embodiments may be directed to generating displays of any internal or external anatomical portions of the human body and/or animal bodies.

The Buffer Zone Engine renders the 3D virtual medical model in an AR display based on the 3D medical model data. In addition, the Buffer Zone Engine renders the 3D virtual medical model based on model pose data which describes an orientation and position of the rendering of the 3D virtual medical model. The Buffer Zone Engine applies the model pose data to the 3D medical model data to determine one or more positional coordinates in the unified 3D coordinate system for portion(s) of model data of a slice layer(s) that represent various anatomical locations.

The Buffer Zone Engine further renders the 3D virtual medical model based on a current device pose of an AR headset device worn by the user. The current device pose represents a current position and orientation of the AR headset device in the physical world. The Buffer Zone Engine translates the current device pose to a position and orientation within the unified 3D coordinate system to determine the user's perspective view of the AR display. The Buffer Zone Engine generates a rendering of the 3D virtual medical model according to the model pose data for display to the user in the AR display according to the user's perspective view. Similarly, the Buffer Zone Engine generates instrument pose data based on a current pose of a physical instrument. The current instrument pose represents a current position and orientation of a physical instrument in the physical world. For example, the physical instrument may be held by a user's hands and may have one or more fiducial markers. The Buffer Zone Engine translates the current instrument pose to a position and orientation within the unified 3D coordinate system to determine the physical instrument's display position and orientation in the AR display and/or placement with respect to one or more virtual objects. It is understood that the Buffer Zone Engine continually updates the instrument pose data to represent subsequent changes in the position and orientation of the physical instrument.

Various embodiments described herein provide functionality for selection of menu functionalities and positional display coordinates. For example, the Buffer Zone Engine tracks one or more physical gestures such as movement of a user's hand(s) and/or movement of a physical instrument (s) via one or more tracking algorithms to determine directional data to further be utilized in determining whether one or more performed physical gestures indicate a selection of one or more types of functionalities accessible via the AR display and/or selection and execution of a virtual interaction(s). For example, the Buffer Zone Engine may track movement of the user's hand that results in movement of a physical instrument and/or one or more virtual offsets and virtual objects associated with the physical instrument. The Buffer Zone Engine may determine respective positions and changing positions of one or more hand joints or one or more portions of the physical instrument. In various embodiments, the Buffer Zone Engine may implement a simultaneous localization and mapping (SLAM) algorithm.

The Buffer Zone Engine may generate directional data based at least in part on average distances between the user's palm and the user's fingers and/or hand joints or distances between portions (physical portions and/or virtual portions) of a physical instrument. In some embodiments, the Buffer Zone Engine generates directional data based on detected directional movement of the AR headset device worn by the user. The Buffer Zone Engine determines that the directional data is based on a position and orientation of the user's hand(s) (or the physical instrument) that indicates a portion (s) of a 3D virtual object with which the user seeks to select and/or virtually interact with and/or manipulate.

According to various embodiments, the Buffer Zone Engine may implement a collision algorithm to determine a portion of a virtual object the user seeks to select and/or virtually interact with. For example, the Buffer Zone Engine may track the user's hands and/or the physical instrument according to respective positional coordinates in the unified 3D coordinate system that correspond to the orientation of the user's hands and/or the physical instrument in the physical world. The Buffer Zone Engine may detect that one or more tracked positional coordinates may overlap (or be the same as) one or more positional coordinates for displaying a particular portion(s) of a virtual object. In response to detecting the overlap (or intersection), the Buffer Zone Engine determines that the user seeks to select and/or virtually interact with the portion(s) of the particular virtual object displayed at the overlapping positional coordinates.

According to various embodiments, upon determining the user seeks to select and/or virtually interact with a virtual object, the Buffer Zone Engine may detect one or more changes in hand joint positions and/or physical instrument positions and identify the occurrence of the position changes as a performed selection function. For example, a performed selection function may represent an input command to the Buffer Zone Engine confirming the user is selecting a portion of a virtual object via a ray casting algorithm and/or collision algorithm. For example, the performed selection function may also represent an input command to the Buffer Zone Engine confirming the user is selecting a particular type of virtual interaction functionality. For example, the user may perform a physical gesture of tips of two fingers touching to correspond to a virtual interaction representing an input command, such as a select input command.

The Buffer Zone Engine identifies one or more virtual interactions associated with the detected physical gestures. In various embodiments, the Buffer Zone Engine identifies a virtual interaction selected by the user, or to be performed by the user, based on selection of one or more functionalities from a 3D virtual menu displayed in the AR display. In addition, the Buffer Zone Engine identifies a virtual interaction selected by the user according to one or more predefined gestures that represent input commands for the Buffer Zone Engine. In some embodiments, a particular virtual interaction may be identified based on a sequence of performed physical gestures detected by the Buffer Zone Engine. In some embodiments, a particular virtual interaction may be identified as being selected by the user based on a series of preceding virtual interactions. As shown in the flowchart 200 of FIG. 2, at step 202, the Buffer Zone Engine renders an Augmented Reality (AR) display, a dynamic navigation guide virtual object ("dynamic navigation guide").

At step 204, the Buffer Zone Engine detects one or more changes in at least one of an instrument angular distance and an instrument position of a physical instrument in a unified three-dimensional (3D) coordinate space.

At step 206, the Buffer Zone Engine determines the one or more detected changes correspond to a threshold amount of difference away from a proper alignment of the physical instrument, the proper alignment representing alignment of the physical instrument with a virtual trajectory towards a target point.

At step 208, Buffer Zone Engine triggers a type of visual characteristic(s) of the dynamic navigation guide in response to determining the one or more detected changes correspond to the threshold amount of difference away from the proper alignment.

According to various embodiments, if proper alignment between the physical instrument and a path of the virtual trajectory requires both an instrument angular distance X and a position Y, then the Buffer Zone Engine detect misalignment when a current instrument angular distance>X and a current instrument position>Y.

The Buffer Zone Engine thereby defines an alignment zone as an angular distance from 0 to X and a position from 0 to Y. The Buffer Zone Engine thereby defines a buffer zone within the alignment zone. The Buffer Zone Engine thereby detects that the physical instrument qualifies for being in the buffer zone when a current instrument angular distance<X and a current instrument position is between Y−0.5 and Y (i.e., a range from Y minus 0.5 to . . . Y). In addition, the Buffer Zone Engine also detects that the physical instrument qualifies for being in the buffer zone when a current instrument angular distance X−0.5 and X (i.e., a range from X minus 0.5 to . . . X) and a current instrument position is Y.

Figure 3:
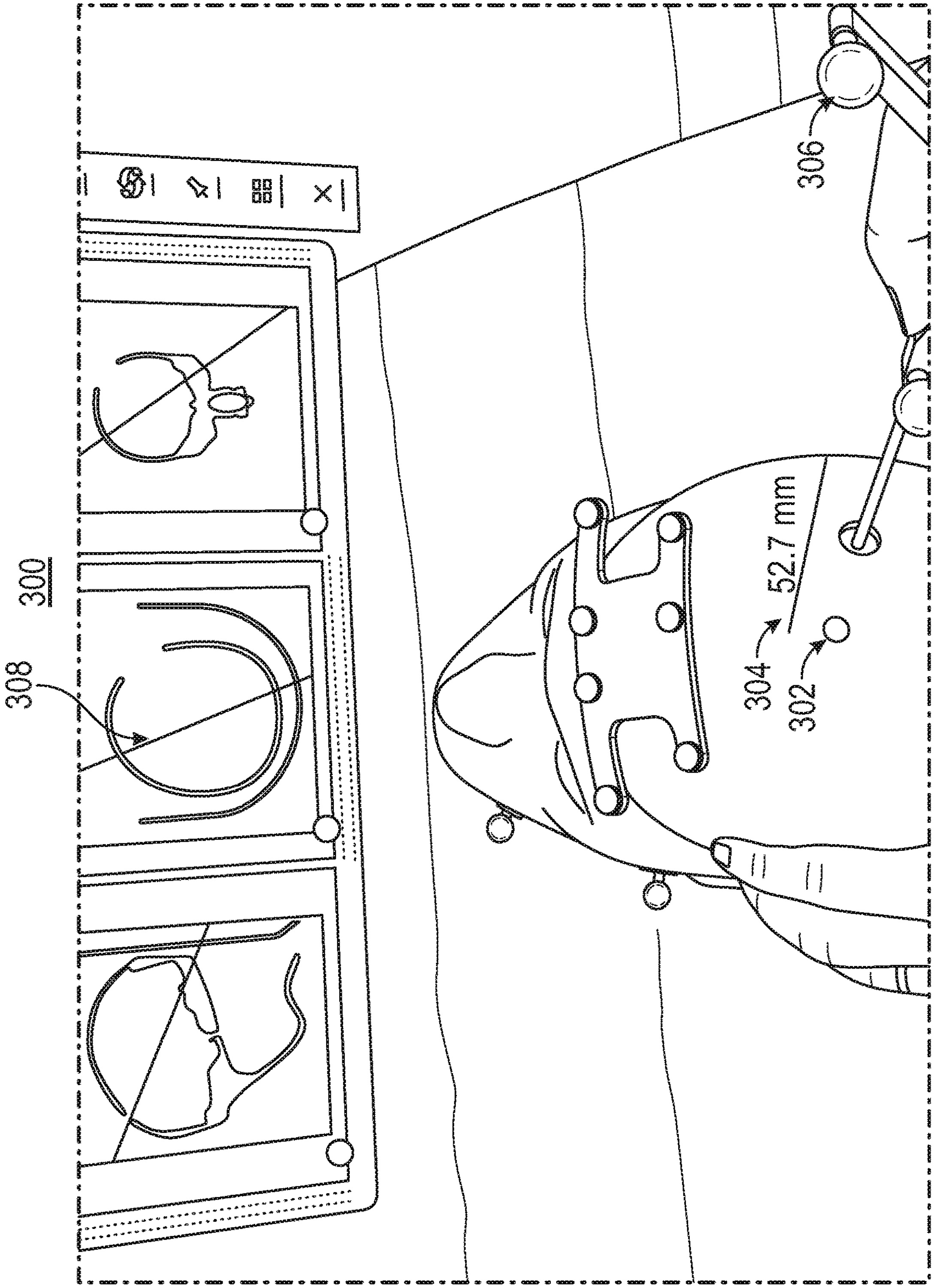
FIG. 3 is a diagram illustrating an exemplary environment in which some embodiments may operate.

As shown in FIG. 3, the Buffer Zone Engine generates and renders an AR display 300 that includes display of a first dynamic navigation guide 302 ("first guide") and a second dynamic navigation guide 304 ("second guide") The AR display may further include a display of a physical instrument 306. It is understood that the AR display may further include a virtual representation of the physical instrument 306 that may also include one or more virtual overlays.

In various embodiments, a virtual trajectory 308 may also be represented in the AR display. In some embodiments, the virtual trajectory 308 extends from a target point such that the Buffer Zone Engine renders the virtual trajectory 308 as passing through an entry point on a 3D virtual medical model. For example, the entry point may be a selected portion of a 3D virtual medical model that represents a physical anatomical feature that has been identified as a location on a surface of an anatomical region. In some embodiments, display of the virtual trajectory 308 may include a solid line portion and a dashed line portion.

According to various embodiments, the Buffer Zone Engine may render the first guide 302 as a circle aim with a first and second component. The first component of the circle aim may be a circle that surrounds a second component, which is a circle aim target. The circle aim target may be rendered by the Buffer Zone Engine as a filled circle (such as, for example, a dot) that changes its display position to represent respective changes in a current angular distance of the physical instrument 306.

According to various embodiments, the Buffer Zone Engine may render the second guide 304 as a virtual line object. The second guide 304 may be rendered to reflect changes in the position (i.e. physical orientation) of the physical instrument 306, such as a distance between a current position of a tip of the physical instrument and a path of the virtual trajectory.

Figure 4:
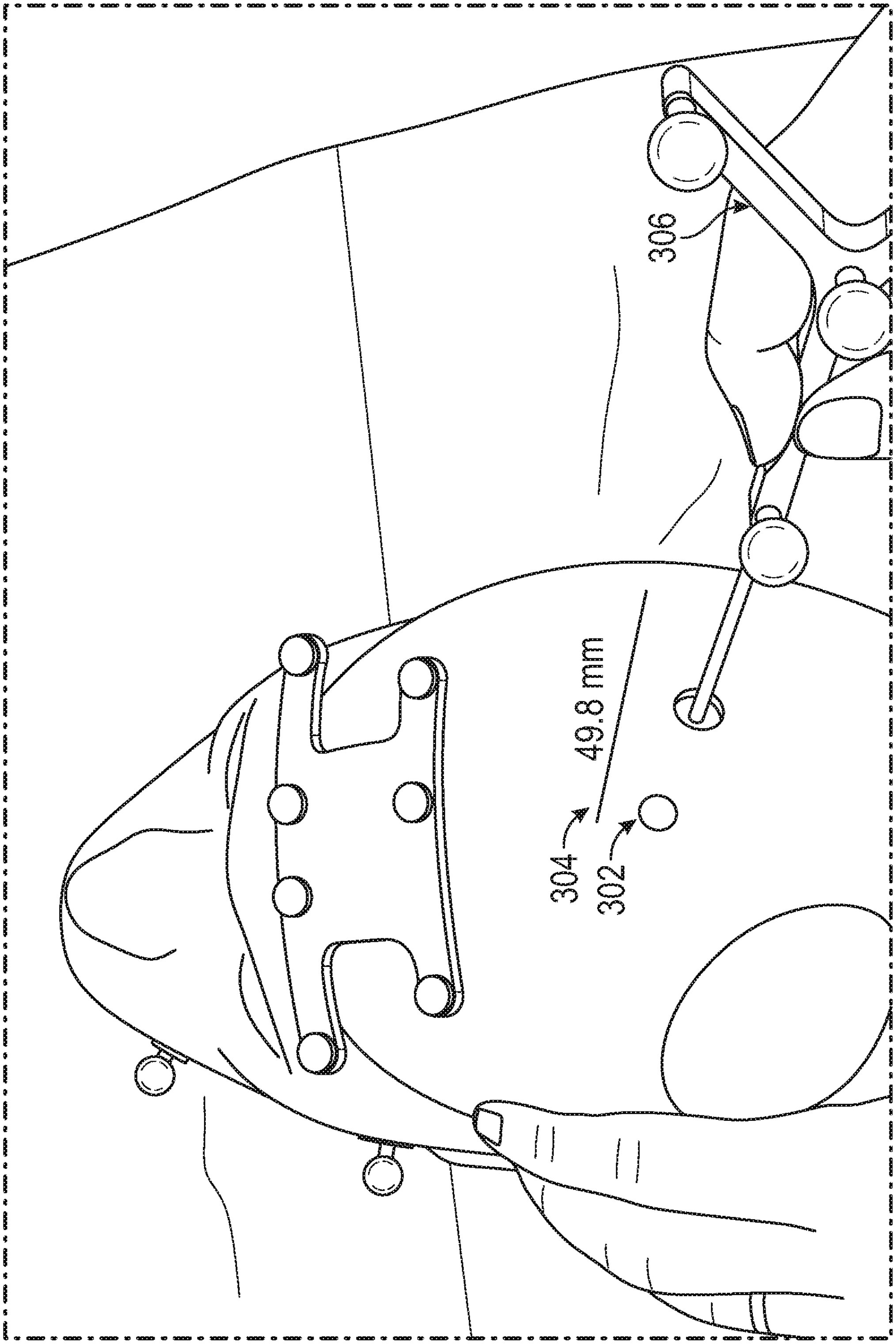
FIG. 4 is a diagram illustrating an exemplary environment in which some embodiments may operate.

As shown in FIG. 4, the Buffer Zone Engine detects movement of the physical instrument 306. The Buffer Zone Engine further determines an extent of alignment between the physical instrument 306 and the virtual trajectory 308 due to one or more changes in the instrument angular distance and/or position. For example, the detected movement results in the physical instrument 306 acquiring an instrument angular distance and/or position (i.e. physical orientation) that sets the physical instrument 306 in near misalignment with the trajectory 308. That is, the current instrument angular distance and/or current position (i.e. physical orientation)—resulting from movement of the physical instrument 306-sets the physical instrument 306 within a buffer zone of an alignment zone. The buffer zone represents a range of instrument angular distances and/or positions that, when detected, indicate that the instrument 306 has been moved away from being in proper alignment with the trajectory 308 and is moving towards misalignment with the virtual trajectory 308.

For example, the buffer zone may have a minimum boundary that corresponds to a certain extent of difference between an instrument's current angular distance and/or current position in comparison with an instrument angular distance and/or position that represents alignment with the trajectory 308. The buffer zone may have a maximum boundary that corresponds to an instrument's current angular distance and/or current position representing the instrument 306 as being in misalignment with the trajectory 308.

Based on detecting movement of the physical instrument 306, the Buffer Zone Engine changes the display position of the second component, the circle aim target, of the first guide 302. For example, the Buffer Zone Engine renders the filled circle (or dot) as moving inside the first guide 302. Upon detecting the instrument's 306 current angular distance is between the minimum and maximum boundaries of the buffer zone while the position of the instrument 306 satisfies a position condition for alignment, the Buffer Zone Engine triggers display of a visual characteristic. For example, the Buffer Zone Engine may change a current color of a portion (s) of the first guide 302. The color change thereby acts as a visual cue to a user manipulating the physical instrument 306 that the physical instrument is no longer in alignment with the trajectory 308 and is in the buffer zone and approaching misalignment.

In some embodiments, the Buffer Zone Engine may also change a current color of a portion(s) of the second guide. 304 The color change of the second guide 304 may also act as a visual cue to a user manipulating the physical instrument 306 that the physical instrument is no longer in alignment with the trajectory 308 and is approaching misalignment. In some embodiments, upon detecting the instrument's 306 current angular distance satisfies an angular distance condition for alignment but the position of the instrument 306 is within the buffer zone for position measurements, Buffer Zone Engine may trigger display of a change a color of the guide 304.

It is understood that Buffer Zone Engine may utilize different types of visual characteristics. A first visual characteristic may be displayed for movement into a first lower boundary of the buffer zone. A second visual characteristic may be displayed for movement between the first lower boundary and a second upper boundary of the buffer zone. A third visual characteristic may be displayed for movement that passes through the second upper boundary of the buffer zone. It is understood that the buffer zone and alignment zone share the same second upper boundary.

Figure 5:
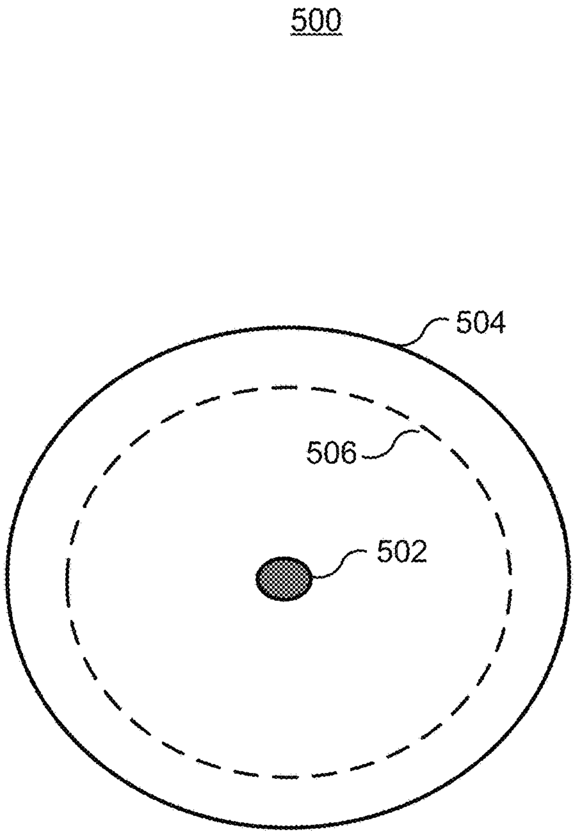
FIG. 5 is a diagram illustrating a design of an exemplary environment according to which some embodiments may operate.

As shown in FIG. 5, a first guide 302 may defined to include an alignment zone that has a radius from the a point 502 on the virtual trajectory's path to an upper boundary 504. A buffer zone may have a lower boundary 506 that falls within the alignment zone. The buffer zone and the alignment zone share the same upper boundary 504.

The Buffer Zone Engine triggers display of a visual characteristic on the first guide 302 when a current position of a physical instrument satisfies an alignment position but a current angular distance of the physical instrument falls between the buffer zone's lower boundary 506 and upper boundary 504.

Figure 6:
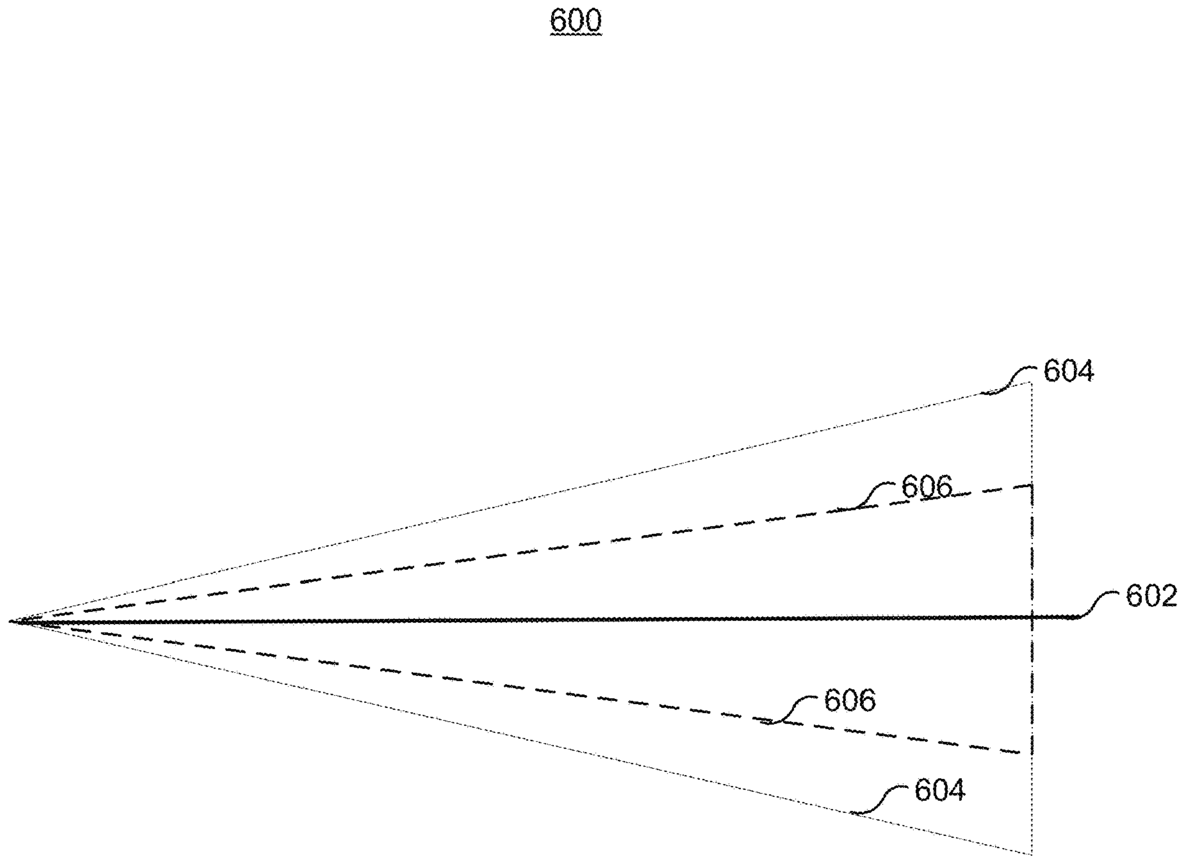
FIG. 6 is a diagram illustrating a design of an exemplary environment according to which some embodiments may operate.

As shown in FIG. 6, a second guide 304 may defined to include an alignment zone that spans a distance between the virtual trajectory's path 602 to an upper boundary 604. A buffer zone may have a lower boundary 606 that falls within the alignment zone. The buffer zone and the alignment zone share the same upper boundary 604.

The Buffer Zone Engine triggers display of a visual characteristic on the second guide 304 when a current angular distance of a physical instrument satisfies an alignment angular distance but a distance between a tip of the instrument and the virtual trajectory's path 602 between the buffer zone's lower boundary 606 and upper boundary 604.

Figure 7:
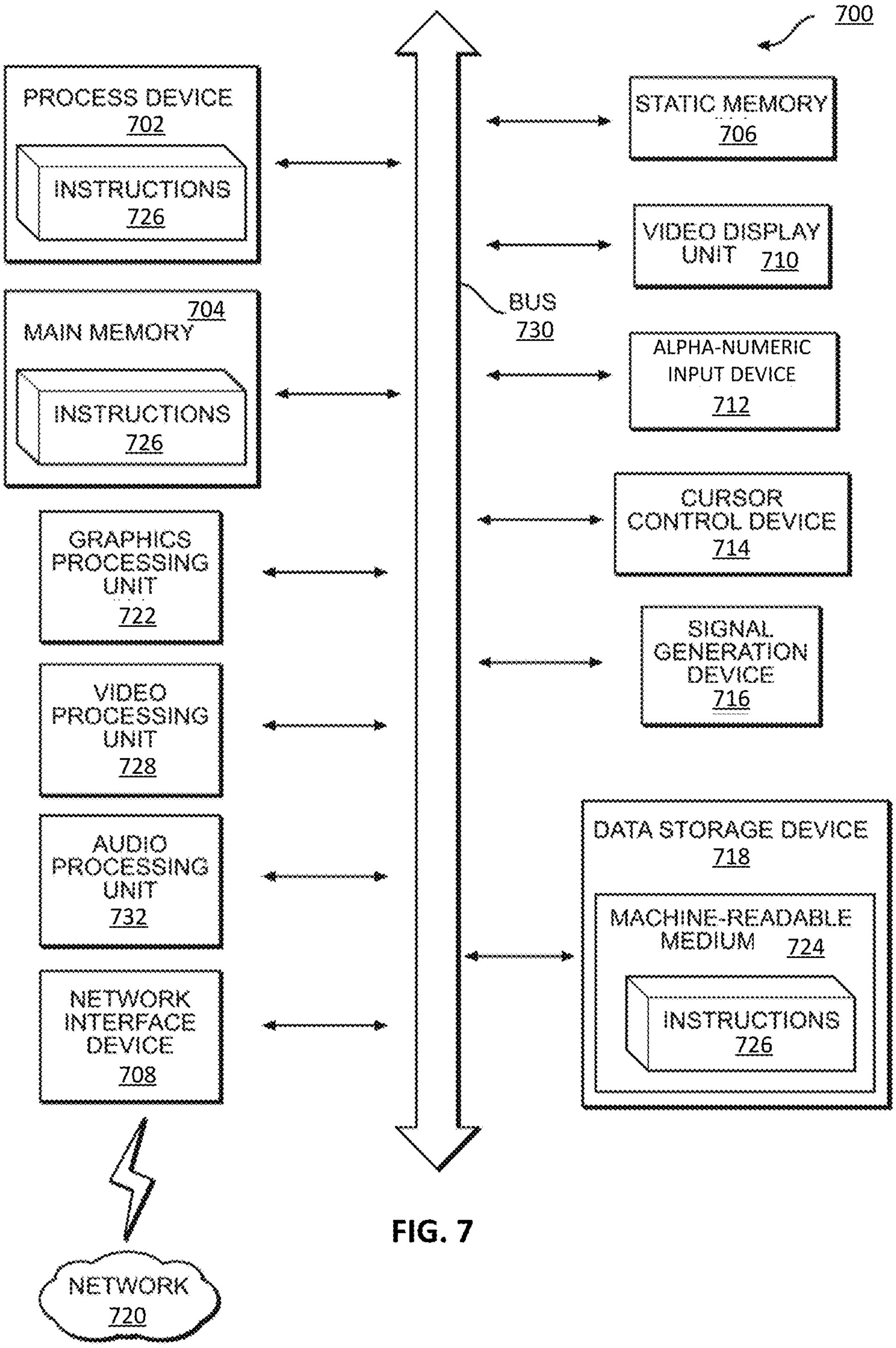
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD- ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:

rendering a three-dimensional virtual medical model in an augmented reality (AR) display;

rendering the three-dimensional virtual medical model, based on a device pose of an AR headset;

determining a user's perspective view in the AR headset by translating the device pose of the AR headset to a device position and device orientation within a unified three-dimensional (3D) coordinate space;

generating a rendering of the user's perspective view in the AR headset;

generating instrument pose data of a physical instrument;

translating the instrument pose data to an instrument position and instrument orientation within the unified 3D coordinate space;

generating a virtual instrument in the AR display, based on the instrument pose data;

rendering, in the AR display, a dynamic navigation guide virtual object;

detecting one or more changes in at least one of an instrument angular distance and the instrument position of the physical instrument in the unified 3D coordinate space, wherein the angular distance is based on a projected distance from a placement of the physical instrument to a virtual trajectory towards a target point and the angular distance is based on an angular difference between at least one axis of the physical instrument at the instrument placement and a corresponding axis of the virtual trajectory;

determining the one or more detected changes correspond to a threshold amount of difference away from a proper alignment of the physical instrument, the proper alignment representing alignment of the physical instrument with the virtual trajectory towards the target point;

triggering a first visual characteristic of the dynamic navigation guide virtual object in response to determining the one or more detected changes corresponding to the threshold amount of difference away from the proper alignment, wherein the dynamic navigation guide virtual object comprises a first component and a second component, the first component surrounding the second component, the second component comprising an aim target; and rendering the second component to change display of the second component in the AR display, to represent respective changes in the angular distance of the physical instrument.

2. The computer-implemented method of claim 1, wherein the threshold amount of difference corresponds to a buffer zone between both the proper alignment of the physical instrument with the virtual trajectory and a misalignment of the physical instrument with the virtual trajectory.

3. The computer-implemented method of claim 2, wherein the buffer zone is defined as a portion of an alignment zone;

wherein a first boundary of the alignment zone represents alignment between a respective physical instrument and a virtual trajectory path and a second boundary of the alignment zone represents misalignment between a respective physical instrument and a virtual trajectory path;

wherein a first boundary of the buffer zone is within the alignment zone and different than the first boundary of the alignment zone; and wherein a second boundary of the buffer zone is the same as the second boundary of the alignment zone.

4. The computer-implemented method of claim 2, further comprising:

maintaining display of the first visual characteristic of the dynamic navigation guide virtual object, while one or more subsequent detected angular distances of the physical instrument continue to fall within boundaries of the buffer zone, wherein a respective angular distance comprises an angular difference between one or more current axis of the physical instrument and one or more of a current axis of the virtual trajectory's path.

5. The computer-implemented method of claim 2, further comprising:

maintaining display of the first visual characteristic of the dynamic navigation guide virtual object, while one or more subsequent detected positions of the physical instrument continue to fall within boundaries of the buffer zone, the respective subsequent detected positions representing a distance between a tip of the physical instrument and the virtual trajectory's path.

6. The computer-implemented method of claim 1, wherein triggering the first visual characteristic of the dynamic navigation guide virtual object comprises:

changing at least a portion of the dynamic navigation guide virtual object, according to the first visual characteristic.

7. The computer-implemented method of claim 1, further comprising:

terminating display of the first visual characteristic in response to determining one or more subsequent changes in at least one of: (a) the instrument angular distance and the (b) instrument position of the physical instrument exceeds a shared boundary of a buffer zone and an alignment zone.

8. The computer-implemented method of claim 7, further comprising:

triggering display of a second visual characteristic in response to determining one or more subsequent changes in at least one of: (a) the instrument angular distance and the (b) instrument position of the physical instrument exceeds the shared boundary of a buffer zone and an alignment zone.

9. A system comprising one or more processors, and a non-transitory computer-readable medium including one or more sequences of instructions that, when executed by the one or more processors, cause the system to perform operations comprising:

rendering a three-dimensional virtual medical model in an augmented reality (AR) display;

rendering the three-dimensional virtual medical model, based on a device pose of an AR headset;

determining a user's perspective view in the AR headset by translating the device pose of the AR headset to a device position and device orientation within a unified three-dimensional (3D) coordinate space;

generating a rendering of the user's perspective view in the AR headset;

generating instrument pose data of a physical instrument;

translating the instrument pose data to an instrument position and instrument orientation within the unified 3D coordinate space;

generating a virtual instrument in the AR display, based on the instrument pose data;

rendering, in the AR display, a dynamic navigation guide virtual object;

detecting one or more changes in at least one of an instrument angular distance and the instrument position of the physical instrument in the unified 3D coordinate space, wherein the angular distance is based on a projected distance from a placement of the physical instrument to a virtual trajectory towards a target point and the angular distance is based on an angular difference between at least one axis of the physical instrument at the instrument placement and a corresponding axis of the virtual trajectory;

determining the one or more detected changes correspond to a threshold amount of difference away from a proper alignment of the physical instrument, the proper alignment representing alignment of the physical instrument with the virtual trajectory towards the target point;

triggering a first visual characteristic of the dynamic navigation guide virtual object in response to determining the one or more detected changes corresponding to the threshold amount of difference away from the proper alignment, wherein the dynamic navigation guide virtual object comprises a first component and a second component, the first component surrounding the second component, the second component comprising an aim target; and rendering the second component to change display of the second component in the AR display, to represent respective changes in the angular distance of the physical instrument.

10. The system of claim 9, wherein the threshold amount of difference corresponds to a buffer zone between both the proper alignment of the physical instrument with the virtual trajectory and a misalignment of the physical instrument with the virtual trajectory.

11. The system of claim 10, wherein the buffer zone is defined as a portion of an alignment zone;

wherein a first boundary of the alignment zone represents alignment between a respective physical instrument and a virtual trajectory path and a second boundary of the alignment zone represents misalignment between a respective physical instrument and a virtual trajectory path;

wherein a first boundary of the buffer zone is within the alignment zone and different than the first boundary of the alignment zone; and wherein a second boundary of the buffer zone is the same as the second boundary of the alignment zone.

12. The system of claim 10, further comprising:

maintaining display of the first visual characteristic of the dynamic navigation guide virtual object, while one or more subsequent detected angular distances of the physical instrument continue to fall within boundaries of the buffer zone.

13. The system of claim 10, further comprising:

maintaining display of the first visual characteristic of the dynamic navigation guide virtual object, while one or more subsequent detected positions of the physical instrument continue to fall within boundaries of the buffer zone, the respective subsequent detected positions representing a distance between a tip of the physical instrument and the virtual trajectory's path.

14. The system of claim 9, wherein triggering the first visual characteristic of the dynamic navigation guide virtual object comprises:

changing at least a portion of the dynamic navigation guide according to the first visual characteristic.

15. The system of claim 9, further comprising:

terminating display of the first visual characteristic in response to determining one or more subsequent changes in at least one of: (a) the instrument angular distance and the (b) instrument position of the physical instrument exceeds a shared boundary of a buffer zone and an alignment zone.

16. The system of claim 15, further comprising:

triggering display of a second visual characteristic in response to determining one or more subsequent changes in at least one of: (a) the instrument angular distance and the (b) instrument position of the physical instrument exceeds the shared boundary of a buffer zone and an alignment zone.

17. A computer program product comprising a non-transitory computer-readable medium having a computer-readable program code embodied therein to be executed by one or more processors, the program code including instructions to:

rendering a three-dimensional virtual medical model in an augmented reality (AR) display;

rendering the three-dimensional virtual medical model, based on a device pose of an AR headset;

determining a user's perspective view in the AR headset by translating the device pose of the AR headset to a device position and device orientation within a unified three-dimensional (3D) coordinate space;

generating a rendering of the user's perspective view in the AR headset;

generating instrument pose data of a physical instrument;

translating the instrument pose data to an instrument position and instrument orientation within the unified 3D coordinate space;

generating a virtual instrument in the AR display, based on the instrument pose data;

rendering, in the AR display, a dynamic navigation guide virtual object;

detecting one or more changes in at least one of an instrument angular distance and the instrument position of the physical instrument in the unified 3D coordinate space, wherein the angular distance is based on a projected distance from a placement of the physical instrument to a virtual trajectory towards a target point and the angular distance is based on an angular difference between at least one axis of the physical instrument at the instrument placement and a corresponding axis of the virtual trajectory;

determining the one or more detected changes correspond to a threshold amount of difference away from a proper alignment of the physical instrument, the proper alignment representing alignment of the physical instrument with the virtual trajectory towards the target point;

triggering a first visual characteristic of the dynamic navigation guide virtual object in response to determining the one or more detected changes corresponding to the threshold amount of difference away from the proper alignment, wherein the dynamic navigation guide virtual object comprises a first component and a second component, the first component surrounding the second component, the second component comprising an aim target; and rendering the second component to change display of the second component in the AR display, to represent respective changes in the angular distance of the physical instrument.

18. The system of claim 17, wherein the threshold amount of difference corresponds to a buffer zone between both the proper alignment of the physical instrument with the virtual trajectory and a misalignment of the physical instrument with the virtual trajectory.

19. The system of claim 18, wherein the buffer zone is defined as a portion of an alignment zone;

wherein a first boundary of the alignment zone represents alignment between a respective physical instrument and a virtual trajectory path and a second boundary of the alignment zone represents misalignment between a respective physical instrument and a virtual trajectory path;

wherein a first boundary of the buffer zone is within the alignment zone and different than the first boundary of the alignment zone; and wherein a second boundary of the buffer zone is the same as the second boundary of the alignment zone.

20. The system of claim 18, further comprising:

maintaining display of the first visual characteristic of the dynamic navigation guide virtual object, while one or more subsequent detected angular distances of the physical instrument continue to fall within boundaries of the buffer zone.

* * * * *